US010078072B2

(12) United States Patent
Leckebusch et al.

(10) Patent No.: US 10,078,072 B2
(45) Date of Patent: Sep. 18, 2018

(54) SAMPLE DISPENSER FOR AN ANALYTICAL DEVICE

(71) Applicant: HAMILTON BONADUZ AG, Bonaduz (CH)

(72) Inventors: Klaus Leckebusch, Masein (CH); Tino Otte, Berschis (CH)

(73) Assignee: HAMILTON BONADUZ AG, Bonaduz (CH)

( * ) Notice: Subject to any disclaimer, the term of this patent is extended or adjusted under 35 U.S.C. 154(b) by 261 days.

(21) Appl. No.: 14/888,366

(22) PCT Filed: Mar. 31, 2014

(86) PCT No.: PCT/EP2014/056432
§ 371 (c)(1),
(2) Date: Oct. 30, 2015

(87) PCT Pub. No.: WO2014/177331
PCT Pub. Date: Nov. 6, 2014

(65) Prior Publication Data
US 2016/0077062 A1 Mar. 17, 2016

(30) Foreign Application Priority Data

Apr. 30, 2013 (DE) .................. 10 2013 104 404

(51) Int. Cl.
*G01N 30/20* (2006.01)
*G01N 35/10* (2006.01)
*G01N 30/06* (2006.01)

(52) U.S. Cl.
CPC ............ *G01N 30/20* (2013.01); *G01N 30/06* (2013.01); *G01N 35/1097* (2013.01); *G01N 2030/204* (2013.01)

(58) Field of Classification Search
CPC ...................................................... G01N 30/20
See application file for complete search history.

(56) References Cited

U.S. PATENT DOCUMENTS 3,022,673 A * 2/1962 Fuller ...................... F16K 3/26
73/863.73
3,100,984 A 8/1963 Martin
(Continued)

FOREIGN PATENT DOCUMENTS

| DE | 10 2007 000 622 A1 | 5/2008 |
| EP | 1 128 109 A1 | 8/2001 |
| WO | 2010/084180 A1 | 7/2010 |

*Primary Examiner* — Robert R Raevis
(74) *Attorney, Agent, or Firm* — Seed IP Law Group LLP

(57) ABSTRACT

A sample dispenser for an analysis device, in particular for an analysis device working according to the principle of liquid chromatography, in particular high pressure liquid chromatography, or gas chromatography, comprising a sample intake for receiving a sample to be analyzed, an inlet through which an eluent can be supplied, an outlet, and an injection valve arrangement, which can be switched at least from an intake position to an injection position, wherein, at least in the intake position and in the injection position, the inlet is in fluid connection with the outlet to deliver the eluent—if applicable, having the sample added thereto—at least partly to the outlet, wherein, in the intake position, the sample intake is separated from the eluent in a fluid-tight manner, and wherein, in the injection position, the sample in the sample intake can combine with the eluent, wherein the sample dispenser is configured as a disposable component.

28 Claims, 10 Drawing Sheets

(56) References Cited

U.S. PATENT DOCUMENTS

| | | | |
|---|---|---|---|
| 3,160,015 A | 12/1964 | Charlton et al. | |
| 3,475,950 A * | 11/1969 | Ferrin | G01N 30/20 73/23.41 |
| 3,918,913 A | 11/1975 | Stevenson et al. | |
| 4,128,008 A | 12/1978 | Linenberg | |
| 6,632,404 B1 | 10/2003 | Freitag et al. | |
| 8,414,832 B1 * | 4/2013 | Roques | G01N 30/30 422/89 |
| 8,944,102 B1 * | 2/2015 | Wiederin | F16K 11/0743 137/625.46 |
| 2014/0053930 A1 * | 2/2014 | Schubert | F16K 11/0743 137/625 |

* cited by examiner

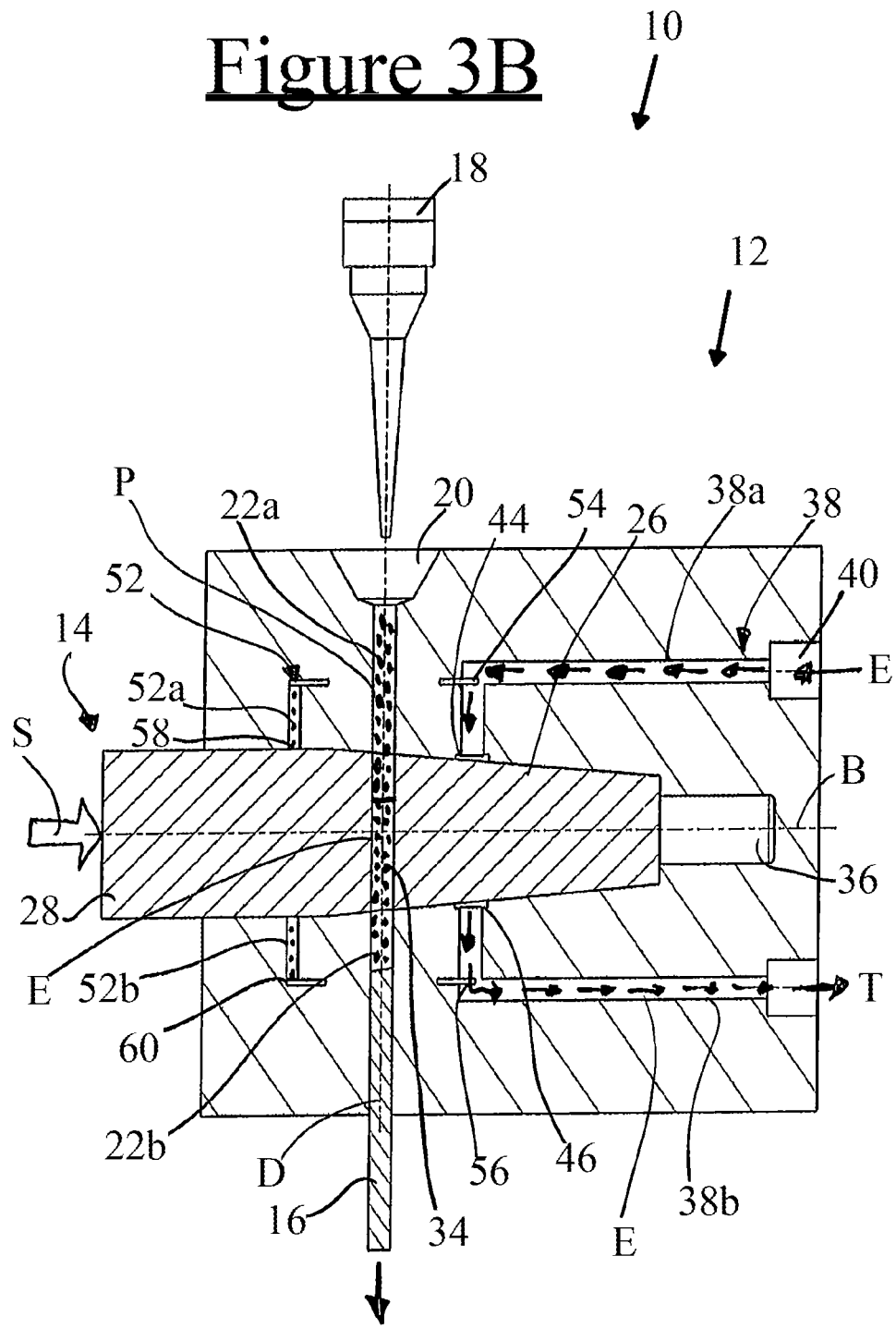

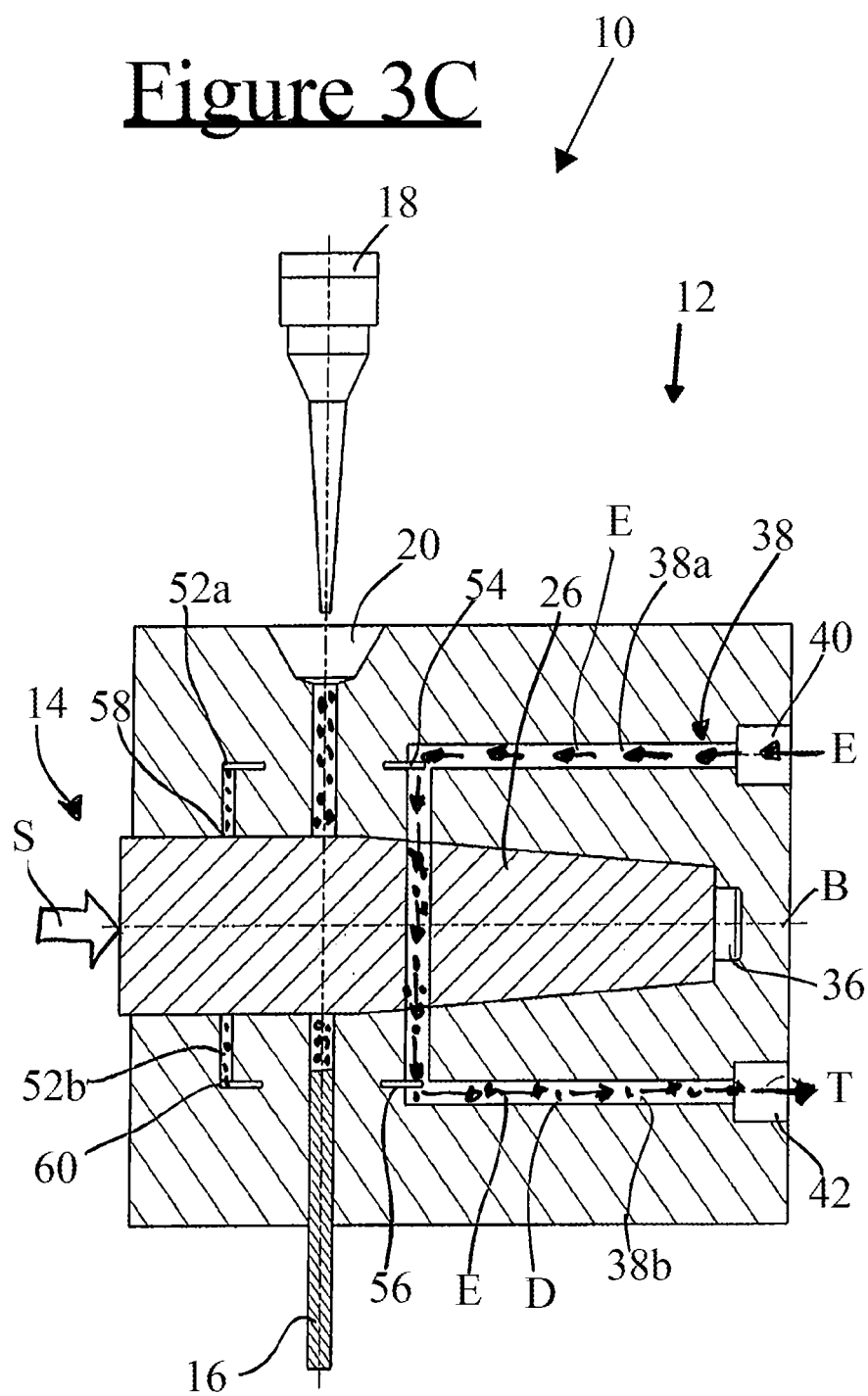

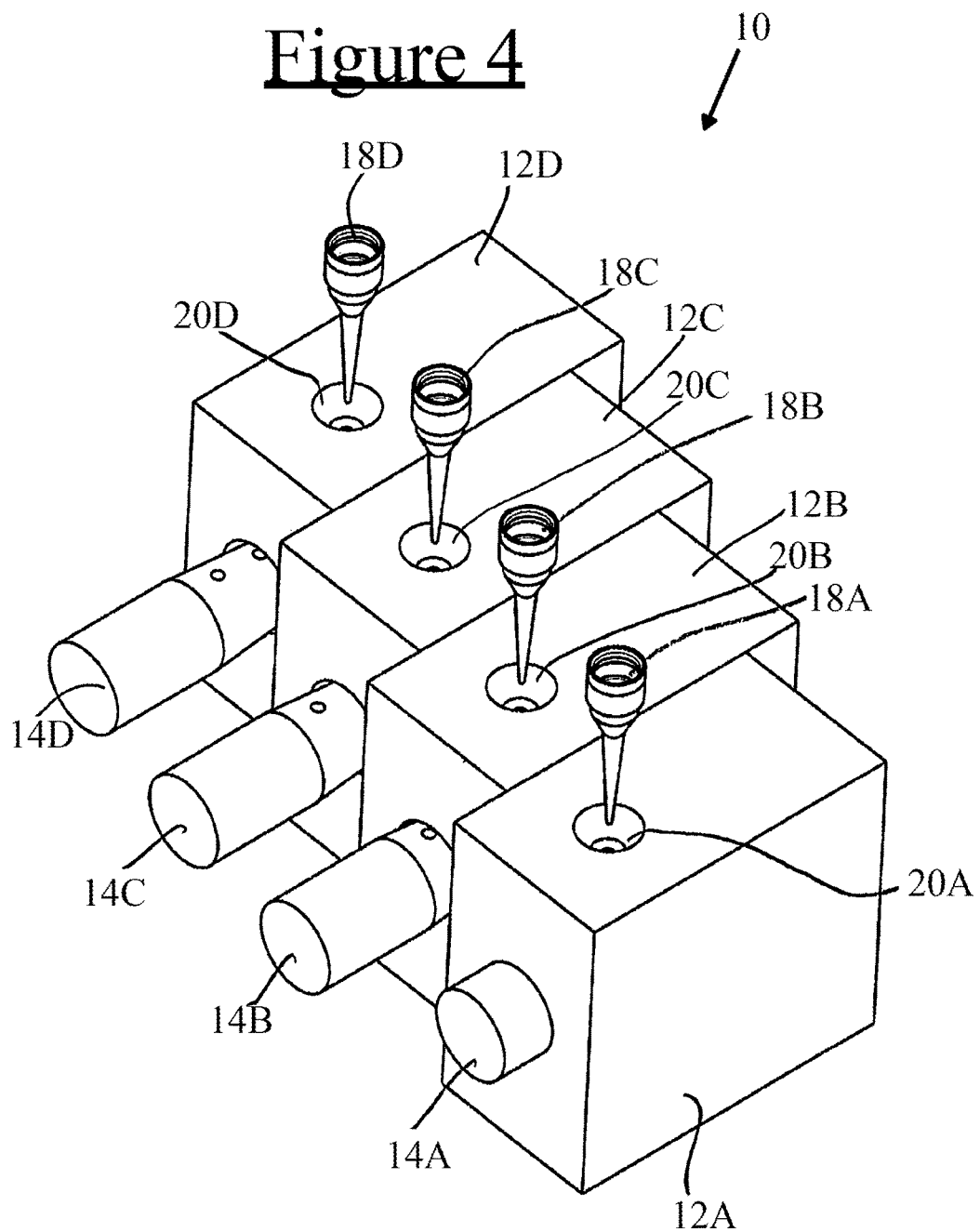

SAMPLE DISPENSER FOR AN ANALYTICAL DEVICE

BACKGROUND

Technical Field

The present invention relates to a sample dispenser for an analysis device for analyzing a liquid or gaseous sample, in particular to an analysis device operating according to the principle of chromatography.

Description of the Related Art

The invention is in particular applicable in the field of liquid chromatography (LC), high performance liquid chromatography (HPLC) or gas chromatography (GC).

Nowadays, liquid chromatography, high performance liquid chromatography (HPLC) or gas chromatography use a fixed high-pressure injection valve for sample injection. The high-pressure injection valve is typically a rather complex component, which comprises several ports and can be switched between an intake position and an injection position. To render the analyses as accurate as possible, it is necessary to evenly apply a mobile phase to the respectively utilized separating columns. It is therefore important that the switching of the injection valve affects the flow of the mobile phase over the separating column as minimally as possible. Furthermore, possible contamination sources must of course be eliminated to the greatest extent possible. This is especially problematic when many samples are to be analyzed successively.

U.S. Pat. No. 3,918,913 shows an example of a common sample dispenser system used in liquid chromatography, in which a so-called 6-port valve is used for sample injection. The 6-port valve has a substantially rotational-symmetric configuration with a valve body and an actuator that is rotatable about a valve axis. The valve body is provided with 6 ports, wherein two selected adjacent ports can be connected with each other by rotating the actuator. A first port of the valve body constitutes an eluent inlet, i.e., via this port, eluent, which constitutes the mobile phase flowing over the separating column—if applicable, having a substance to be analyzed added thereto—is supplied. Another port of the valve body is associated with the separating column, i.e., constitutes a column outlet for supplying an eluent, or an eluent having a substance to be analyzed added thereto, to the separating column. The other four ports of the valve body are associated with a sample dispenser system. Two of these four ports of the sample dispenser system are in permanent fluid connection via an external sample loop. One port of the sample dispenser system serves as a sample intake for supplying the sample to be analyzed. Another port is typically connected to a metering pump or the like in order to receive the sample to be analyzed in the sample loop and discharge it again, if applicable.

In an intake position of the injection valve, the eluent inlet is connected with the column outlet and the four ports of the sample dispenser system are interconnected such that a substance to be analyzed (hereinafter also briefly referred to as sample) can be received in the sample loop through the sample inlet. By rotating the injection valve into an injection position, the sample loop can then be switched into fluid connection with the eluent inlet and the column outlet such that the sample is mixed with eluent and reaches the separating column.

In the injection position of the injection valve, surplus sample volume can be removed via the remaining two ports of the sample dispenser system. Before analyzing another sample, the complete sample dispenser system needs to undergo a complex washing procedure to avoid contamination. This is in particular problematic in the region of the sample loop, as impurities remaining in this region directly reach the separating column, while this region can however only be washed by means of the eluent stream, i.e., after injecting the sample and switching the injection valve back to the intake position. In particular in HPLC applications, the contamination of the sample loop is a problem that is difficult to manage, as the sample loop is, in the intake position of the injection valve, filled and washed at relatively low pressures, while in the injection position, it is, however, subject to the high pressure with which the eluent/sample stream is pressed onto the separating column.

A disposable sample intake device which can be used in a sample loop of an injection valve for HPLC is known from DE 10 2007 000 622 A1. Said disposable sample intake device consists of a container for receiving a sample volume, which can be coupled to the sample loop by means of a first coupling arranged on an upstream end of the container and a second coupling arranged on a downstream end of the container. The container is, via the first or the second coupling externally filled with sample volume and then placed in the sample loop by means of the first and the second coupling. The eluent stream is then supplied to the sample loop via the 6-port injection valve. After the analysis is completed, the injection valve is switched back to the intake position and the disposable container in the sample loop can be replaced by a new disposable container containing the next sample to be analyzed. A similar sample dispenser system for HPLC applications is known from WO 2010/084180, in which the pipette tips are adapted to be placed in the sample loop as disposable containers.

BRIEF SUMMARY

One or more embodiments of the present invention provide a sample dispenser for analyzing samples, which has a considerably simpler design while still suppressing contamination effects even when analyzing samples of small and smallest concentrations. The sample dispenser shall in particular be suitable for analyzing liquid or gaseous samples by means of analysis devices using the principle of chromatography, for example high performance liquid chromatography (HPLC), liquid chromatography (LC) or gas chromatography (GC).

According to one embodiment of the present invention, a sample dispenser for an analysis device is provided, in particular for an analysis device using the principle of chromatography (LC), in particular high performance liquid chromatography (HPLC) or gas chromatography (GC), comprising a sample intake for receiving a sample to be analyzed, an inlet through which an eluent can be supplied, an outlet and an injection valve arrangement which can be switched from at least an intake position to an injection position. At least in the intake position and in the injection position, the inlet is in fluid connection with the outlet in order to deliver the eluent—if applicable, having the sample added thereto—at least partly to the outlet. In the intake position, the sample intake is separated from the eluent in a fluid-tight manner, and in the injection position, a sample located in the sample intake can combine with the eluent. The sample dispenser is here configured as a disposable component.

Both the sample loop and the injection valve are thus replaced by a disposable component, which can principally accommodate the complete process of receiving and injecting a sample to be analyzed into the analysis system. This offers the opportunity to exchange the entire sample dispenser for each sample when analyzing many different samples successively. As this procedure allows for disposing, upon completion of analyzing the sample, of virtually all parts which were in contact with the sample, effortful washing procedures, which were absolutely necessitated by conventional sample dispenser systems to reasonably suppress contamination effects between successively analyzed samples, can be eliminated. Contamination between successively analyzed samples can be virtually eliminated even without washing processes.

The sample dispenser is substantially intended for single use, i.e., the injection valve arrangement is adapted to substantially be used only once. Substantially means that even though it is principally possible to switch between the intake position and the injection position repeatedly, such switching back and forth is at any rate not possible an arbitrary number of times or is not possible without having to take certain restrictions into account.

The inlet can be connected to an eluent stream, by which an eluent, which is fed to the analysis device, such as to the separating column of a chromatography device, can be supplied to the sample dispenser as a mobile phase. The outlet is in connection with the analysis device, such as the separating column, such that the eluent—if applicable, having the sample added thereto—can be conveyed from the sample dispenser to the analysis device as a mobile phase. The eluent stream typically only carries, in the intake position of the injection valve arrangement, one eluent, i.e., only one eluent is delivered from the outlet to the analysis device as a mobile phase. In the injection position of the injection valve arrangement, the eluent coming from the eluent inlet is typically mixed with the sample to be analyzed and then delivered as a mobile phase via the outlet to the analysis device.

The sample intake may in particular also be integrated into the disposable component, either as a volume formed in the disposable component or as a separate component which can be connected to the disposable component. To reduce contamination effects, is advisable to configure the sample intake as a disposable component as well.

Particular optional designs of the sample dispenser will be explained in greater detail in the following.

Furthermore, the sample dispenser may comprise a sample port, through which, in the intake position of the injection valve arrangement, the sample to be analyzed can be received in the sample intake. The sample port may be adapted to a respectively applicable sample processing system, for example configured as a seat for receiving pipettes or pipette tips filled with the samples to be analyzed, or may comprise a coupling system for docking specific sample containers. To reduce contamination effects effectively, it is usually advisable to design the sample port as a disposable component as well. The sample port may in the simplest case be configured as an integral part of the sample dispenser. The production can be rendered more flexible by coupling a universally usable sample dispenser with different sample ports.

In specific embodiments, the sample dispenser may comprise a valve body and an actuator that is moveable relative to the valve body. The valve body and the actuator can then interact to realize the injection valve arrangement together. For example, an actuating drive acting on the actuator, in particular an electric servomotor, may be provided to displace the actuator relative to the valve body between the intake position and the injection position. At least one fluid connection may be formed in the actuator and/or between the actuator and the valve body, through which, at least in the intake position of the injection valve arrangement, an eluent can flow. The fluid connection may be part of an eluent passage formed between the eluent inlet and the outlet, through which the eluent can flow from the eluent inlet to the outlet. After switching the injection valve arrangement to the injection position, the fluid connection formed in the actuator and/or between the actuator and the valve body may be modified such that an eluent stream combined with the sample to be analyzed passes through the eluent passage to the outlet.

In many cases, it is possible to form the sample intake at least partially in the actuator. This makes it possible to feed a sample into the sample intake when the actuator is in the intake position, and then feed the sample within the sample intake into the eluent stream only by displacing the actuator.

The valve body may be designed, for example, with at least one flow channel, which—if applicable, in interaction with the actuator—forms, at least in the intake position and in the injection position of the injection valve arrangement, the eluent passage between the eluent inlet and the outlet of the sample dispenser. For example, the flow channel starting from the eluent inlet may feed into the outlet of the sample dispenser when the actuator is in the intake position and when the actuator is in the injection position. It may be advantageous to design the eluent passage by means of the flow channel and at least partially in interaction with the actuator. Then the flow channel can be interrupted by means of the actuator when the actuator is not in the intake position. In particular, the flow channel formed in the intake position may interact with the actuator in such a manner that an eluent passage is formed, so pure eluent from the inlet can be conveyed to the outlet. The flow channel thus formed in the injection position can interact with the actuator such that an eluent/sample passage is formed, through which an eluent having the sample added thereto is conveyed to the outlet.

In many cases, it is advantageous if the injection valve arrangement can also be switched to yet another position in which there is no fluid connection between the inlet and the outlet. Such a position may, for example, be achieved when the flow channel and the actuator interact such that the eluent passage or eluent/sample passage is interrupted. Such a position may be assumed as a substantially transient intermediate position when switching between the intake position and the injection position. In specific cases, it may also be useful to assume such a position permanently, such as after the injection of the sample, to prevent further injection of sample-contaminated fluid through the respective injection valve arrangement. In this case, it is advantageous if the injection valve arrangement can be switched from the injection position to yet another position in which the eluent passage or eluent/sample passage is interrupted. This position can be realized, for example, by displacing the actuator further in the feed direction beyond the injection position. This is useful for example in the case of a sample dispenser having a plurality of injection valve arrangements that are all associated with the same inlet and/or outlet. It is then possible to activate the individual injection valve arrangements one by one, without the need for sophisticated valves in order to avoid cross-contamination effects, as each injection valve arrangement moves, after the injection, into a state in which it is separated from all other valves in a fluid-tight manner.

In some embodiments, the valve body may comprise a cavity in which the actuator is accommodated. The actuator may then, depending on the position relative to the valve body, interact with the inner wall of the valve body surrounding the cavity in order to seal the sample intake in a fluid-tight manner against the eluent passage through which the eluent flows. The actuator and the inner wall of the cavity may also interact such that in another position of the actuator, a fluid-tight seal is also formed, e.g., in order to seal, in the injection position, the sample intake—which then forms a section of the eluent passage between the inlet and the outlet through which the eluent or the sample flows—in a fluid-tight manner against the valve body. The above-mentioned flow channel formed in the valve body preferably transverses the cavity such that by interaction between the flow passage and the actuator, the eluent passage is formed in the intake position and the eluent/sample passage is formed in the injection position.

Moreover, it is favorable if the sample intake comprises a metering chamber arranged in the actuator and/or between the actuator and the valve body, which is in fluid connection or can, in the intake position of the injection valve arrangement, be brought into fluid connection with the sample port. The sample intake can then be constituted by the metering chamber and, optionally, also comprise a channel in particular formed in the valve body, which connects the metering chamber to the sample port. In order to precisely determine the amount or volume of a sample to be analyzed, it is advantageous if the metering chamber has a predetermined volume. This is especially important for quantitative analyses. It is also particularly advantageous if the volume of the sample intake and/or the metering chamber is adjustable such that differently dimensioned samples can be analyzed. For example, the sample dispenser may also comprise a metering chamber or a metering piston interacting with the metering chamber or with the cavity in fluid connection with the metering chamber so as to adjust the volume of the sample intake and/or of the metering chamber. The metering piston may also be associated with an actuator, by means of which the volume of the sample intake and/or the metering chamber can be quantitatively adjusted. The metering piston may be adapted to act on the sample intake and/or the metering piston so as to change the volume thereof when the injection valve arrangement is in the intake position.

In specific embodiments, in particular when a sample to be analyzed has only a small volume or is to be diluted before it is introduced into the eluent stream, it is possible to adapt the sample intake in such a way that it can already be pre-filled with eluent or another fluid prior to introducing the sample into the sample intake. In particular, a partial volume of the metering chamber may then be pre-filled, so only a residual volume needs yet to be filled with the sample introduced through the sample port in order to fill the entire metering chamber. To interfere as little as possible with the fluid stream between the eluent inlet and the outlet when switching between the intake position and the injection position, it is generally preferable to feed the fluid within the metering chamber into the eluent passage formed between the eluent inlet and the outlet in a state that is as similar to the thermodynamic state or flow dynamic state of the eluent stream as possible. In particular, when switching to the injection position, an amount of eluent corresponding to the amount of fluid introduced from the metering chamber should be removed from the eluent flowing in the flow channel or eluent passage. Concerning liquids, this means that the volume of the added fluid (sample, if applicable diluted with more fluid) should equal the volume of eluent to be removed. Alternatively, the volume of the eluent/sample passage may be increased by the volume of the introduced fluid relative to the eluent passage. In particular in case of gases, the introduced volume of gas (sample and, if applicable, eluent) should be introduced with a pressure that is only slightly greater than the pressure prevailing in the eluent passage. If desired, the sample intake may also be pre-filled with a different fluid than the eluent. The pre-filling with fluid or eluent may be carried out in the intake position of the injection valve arrangement or in a specially designated prefill position of the injection valve arrangement, which ensures that the eluent stream supplied to the outlet (which flows over the separating column) is not disturbed during the prefill procedure.

In a simple design, the pre-filling may be carried out via the sample port, in which case the injection valve arrangement may remain in the intake position during the pre-filling procedure.

There are, however, much more possibilities if the injection valve arrangement comprises at least one prefill position in addition to the intake position and the injection position, in which prefill position the sample intake can be filled with eluent or a different fluid. It may be advantageous to carry out the pre-filling not via the sample port but via a specially provided access to the sample intake. To get from the prefill position to receiving the sample to be analyzed, the injection valve arrangement should then at the very least be switchable from the prefill position to the intake position. It is especially preferable if at least part of the sample intake is in fluid connection with the eluent stream when the injection valve arrangement is in the prefill position. This can be realized, for example, by means of a suitable branching from the flow channel connecting the eluent inlet to the outlet. The branching should, in the prefill position, lead into the sample intake, in all other positions, however, be separated from the sample intake in a fluid-tight manner. The branching may, for example, branch off downstream of the eluent inlet and rejoin the flow channel upstream of the point where, in the injection position, the sample to be analyzed is introduced into the eluent stream. Eluent flowing through the branching will then, in the prefill position, flow through the sample intake and in particular fill the metering chamber. If the injection valve arrangement is then switched to the intake position such that the sample intake and/or the metering chamber comes in contact with the sample port, the metering chamber is completely filled with eluent. In this case, a metering element, such as the metering piston mentioned above, may be provided and adapted, in the intake position, to act on the sample intake and/or the metering chamber to vary the volume thereof. In particular, it is favorable, when using such a metering element, that the volume of the sample intake can be increased, with the result that the eluent volume contained in the metering chamber decreases to the extent that the volume of the sample intake through the metering element increases. The resulting residual volume in the metering chamber can then be refilled with the sample. This enables a precise quantitative specification of the sample amount introduced into the metering chamber, such that reproducible quantitative analyses can be conducted even for very small sample volumes.

Furthermore, the actuator may, at least in the intake position of the injection valve arrangement, interact with the valve body such that the sample intake and the eluent passage are, with respect to the eluent and/or the sample, separated in a fluid-tight manner. The actuator will thus in specific regions create a substantially a fluid-tight connection with the valve body, while in other regions expressly allowing a fluid passage, for example between a first part of the flow channel arranged upstream and abutting the eluent inlet and a second part of the flow channel arranged downstream and opening into the outlet.

The actuator may, in particular, be moveable relative to the valve body such that, after switching to the injection position, the sample intake, in particular the metering chamber, comes into fluid connection with the flow channel forming the eluent passage and then, in the injection position, the eluent/sample passage is formed. In cases where the metering chamber is entirely formed in the actuator, this can be realized by placing an end of the metering chamber arranged upstream in fluid connection with the above-mentioned first part of the flow channel arranged upstream and an end of the metering chamber arranged downstream in fluid connection with the aforementioned second part of the flow channel arranged downstream by correspondingly displacing the actuator.

Specific embodiments may provide that the actuator can be moved relative to the valve body along a feed direction, in particular along an axial direction of the actuator, so as to switch the injection valve arrangement from the intake position to the injection position. The actuator is basically pushed or pressed into the valve body. If the injection valve arrangement can be switched from the injection position to yet another position, in which the eluent passage or eluent/sample passage is interrupted, this additional position can also be realized by displacing the actuator further in the feed direction beyond the injection position. This is advantageous in particular if increased displacement of the actuator in the feed direction causes irreversible effects such as plastic deformation of the valve body. Such effects may, when the actuator is displaced in the reverse direction in a per se fluid-tight intermediate position, affect the per se given fluid tightness as the actuator and the valve body are no longer sufficiently pressed together.

It has been found that the required fluid-tightness between the actuator and the valve body can be achieved if the actuator is in a press fit relative to the valve body such that when switching the actuator from the intake position to the injection position, the pressing force does not decrease and preferably increases. Such press fits may be configured in a manner known from the design of control valves in heating, ventilation and air conditioning systems, for example from EP 1 128 109 A1.

In the intake position, it is particularly important that the eluent passage formed between the eluent inlet and the outlet is not blocked while passing the actuator or a region of the actuator interacting with the valve body, while at the same time a fluid-tight separation from the sample intake is created. This requires a relatively loose interaction between the actuator and the valve body in the region of the eluent passage formed between the eluent inlet and the outlet, or a corresponding contouring of the actuator and the valve body in this region, for example, with corresponding recesses and/or elevations on the respective surfaces thereof. However, in a region between the eluent passage and the sample intake, the fit of the actuator in the valve body should be provided in a relatively tight manner in order to ensure the fluid-tightness with respect to the sample intake. After switching to the injection position, a fluid connection between the metering chamber and the flow channel needs to be created such that the sample contained in the metering chamber, optionally already mixed with eluent or other fluid, can be combined with the eluent flowing through the eluent passage. In specific embodiments, the metering chamber replaces a part of the eluent passage to then form the eluent/sample passage. Here, it is important that the eluent/sample passage replaces the eluent passage as seamlessly as possible. For this purpose, the respectively interacting end regions of the metering chamber and the flow channel should connect relatively accurately and as fluid-tightly as possible relative to their environment. This can be realized quite well by providing slightly higher pressing forces. However, it should be ensured that the pressing forces do not become too high, as this might cause the eluent/sample passage formed in the injection position to noticeably narrow relative to the eluent passage.

It turns out that the requirements described can easily be met if the region of the actuator interacting with the valve body has a shape tapered in the feed direction, in particular conically or frusto-conically. Here, the actuator interacts with a correspondingly shaped cavity of the valve body such that the pressing forces acting between the actuator and the valve body generally increase when switching between the intake position and the injection position. An actuator having a tapered cross-section has the feature that the cross-section of the actuator in a plane orthogonal to the feed direction—irrespective of possible structures adapted to form channels—decreases in the feed direction.

To achieve the required fluid-tightness, it may even be envisaged that the pressing forces occurring in the course of switching the injection valve arrangement from the intake position to the injection position cause a deformation of at least the valve body. Normally, it is sufficient if only the valve body is deformed, while the actuator substantially keeps its shape. The deformation may in principle be elastic, such that it can be undone when the pressing forces decrease again, for example in the course of switching the injection valve arrangement from the injection position back to the intake position. It should be noted that embodiment variants of a sample dispenser configured as a non-disposable component and having the remaining features of claim 1 may very well have an independent inventive importance, especially as a replacement for conventionally used injection valves such as those used in chromatography (GC, LC, HPLC). Non-disposable variants may also be further developed for the purpose of the other optional features described herein. Insofar as such non-disposable variants work with pressing forces to achieve the required fluid tightness, it will be desirable to possibly remain in the elastic range, i.e., below or only slightly above the yield strength of the materials used.

If the use of a sample dispenser designed as a disposable component is desirable for reasons of contamination control, at least the valve body may also be provided such as to undergo plastic deformation in the course of switching from the intake position to the injection position. A plastic deformation is here considered a deformation that does not return to its original shape, or at least does not fully retire to its original shape within a short period of time. This will typically occur with pressing forces causing, in a standardized pressure-strain test, a deformation above the yield strength of the respective material.

To set the positional relationship of the actuator relative to the valve body, other embodiments may provide that the region of the actuator interacting with the valve body is formed such that a rotation of the actuator relative to the valve body about the feed axis is suppressed, that is, is at least made difficult, in particular prevented. This can be realized by a suitable surface design of respectively interacting surfaces of the actuator and the valve body. For example, webs or protrusions extending in the feed direction and interacting in the manner of splined toothing are advantageous. The shape of the actuator in a plane orthogonal to the feed direction thereof may also deviate from a circular symmetry (for example by flattening on at least one side, having an ellipse or other geometric shape) such that only specific rotational positions, in particular only one single rotational position, of the actuator relative to the valve body are possible.

The actuator may also be provided such as to be rotated relative to the valve body about the feed axis in a predetermined manner and in relation to an increasing displacement in the feed direction by providing threads in the region of the actuator interacting with the valve body. Such a design allows for higher pressing forces and an improved abutment of the actuator on the valve body with smaller actuating forces acting in the feed direction.

A corresponding surface design of mutually corresponding surfaces of the actuator and/or the valve body may also serve to define specific positions of the actuator and the valve body relative to one another. For example, protrusions projecting transversely to the feed direction or recesses formed on the actuator may serve to define the intake position, the injection position and, optionally, additional positions of the injection valve arrangement. Such protrusions or recesses may interact with the valve body as stops or latches when the respective position has been reached. A specific force is required to move the actuator beyond the predetermined position or, if applicable, to move it back to the original direction thereof. Alternatively or additionally, the respective positions of the injection valve arrangement may be defined using a suitable control of the actuator, since the intake position, the injection position and optionally provided further positions typically are associated with a particular position in the feed direction.

Especially for forming a press fit of the type described above, the actuator and the valve body should typically be made of materials compatible with each other. In many cases, it will be advantageous to produce the actuator from a harder material than the valve body. The valve body may, e.g., be made of a suitable plastic, such as polyetheretherketone (PEEK). Even a relatively soft metal such as aluminum (Al) may be considered. For the actuator, harder materials such as ceramic or steel are suitable, in particular stainless and/or hardened and tempered steel. In the case of a valve body made of a relatively soft material, aluminum is also an option.

For applications in which a plurality of samples is to be analyzed in a relatively short time, a sample dispenser of the type described herein may also be provided with a plurality of actuators, wherein each of the actuators is associated with a respective sample intake. Such sample dispenser may comprise one single valve body having a plurality of cavities or intakes, each of which interacts with one of the actuators. The respective actuators are activated successively and used for injection of a particular sample for the analysis device.

The construction of a sample dispenser as described above allows for an excellent sealing of the fluid passages formed between a respective actuator and the valve body. This applies to the intake position, the injection position and the prefill position, if provided. Also in the intermediate positions of the injection valve arrangement assumed while switching between said positions, the individual fluid passages can be efficiently sealed from one another. This makes it possible to associate several of said actuators, in particular all the actuators, in a sample dispenser with the same eluent inlet and the same outlet. This considerably facilitates the connection to an analysis device. The operation thereof is also very simple, as no additional valves are required for switching from sample injection by one of the actuators to sample injection by another actuator. For this purpose, it is only necessary to initially place the respective next actuator in the intake position thereof, add the sample to be analyzed and then place the actuator in the injection position. In order to suppress contamination effects as efficiently as possible, it is advisable to place a respective actuator, after injection, in a position in which the eluent passage or eluent/sample passage associated with the respective actuator, is sealed in a fluid-tight manner relative to the eluent passages or eluent/sample passages associated with the remaining actuators. It is also possible to place all the actuators independently in the intake position and then apply the sample to be analyzed thereto. It only needs to be ensured that always only one of the actuators is in the injection position.

Embodiments of present invention also relate to an analysis device for analyzing a liquid or gaseous sample, which is adapted to interact with a sample dispenser of the type described above. Such an analysis device may work in particular according to the principle of gas chromatography or the principle of liquid chromatography, in particular high performance liquid chromatography (HPLC). Since the sample dispenser already comprises the injection valve in the form of a disposable component, the analysis device does not need to have its own injection valve. The previously required 6-port valves or even more complex valves are no longer necessary.

The invention also relates to an analysis system comprising at least one sample dispenser of the type described above and at least one analysis device of the type described above.

BRIEF DESCRIPTION OF THE SEVERAL VIEWS OF THE DRAWINGS

The invention will be explained in greater detail below with reference to the drawings, in which:

FIG. 3B shows a further schematic illustration of the sample dispenser of FIG. 3A in the intake position;

FIG. 3C shows a further schematic illustration of the sample dispenser of FIG. 3A in the injection position; and FIG. 4 shows a simplified schematic illustration of a fourth embodiment of an inventive sample dispenser having a plurality of actuators.

DETAILED DESCRIPTION

In all figures, identical or similar components are, irrespective of whether referring to the same or to different embodiments, designated by the same reference signs. A detailed description of the respective components is in each case only given with respect to the embodiment described first. Subsequent embodiments are then always only described explicitly to the extent that they differ from the preceding embodiments. Such differences are designated in the figures by their own reference numbers. Unless otherwise expressly noted, the same description for the preceding embodiment(s) also applies to components of subsequent embodiments that are referred to with the same reference signs as they are in the preceding embodiments. To avoid repetitions, reference is here expressly made to said description.

Figure 1A:
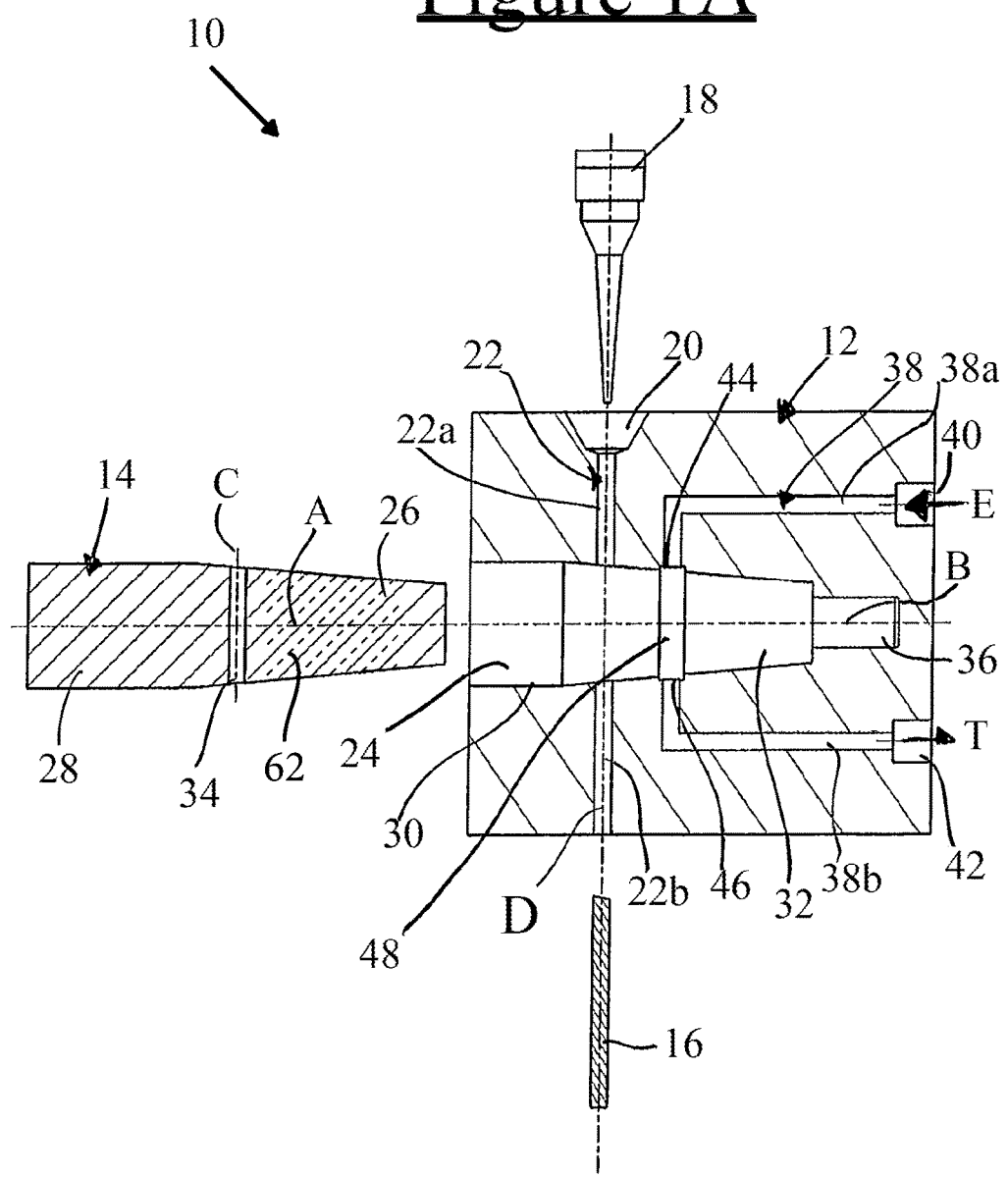
FIG. 1A shows a simplified schematic illustration of a first embodiment of a sample dispenser according to the invention showing the main components prior to assembly.

FIG. 1A shows a simplified schematic illustration of a first embodiment of a sample dispenser 10 according to the invention. The individual components are in FIG. 1A shown in an exploded view in a state prior to final assembly. The sample dispenser 10 comprises a valve body 12, an actuator 14 and a plug 16. Furthermore, FIG. 1A schematically indicates at 18 a pipette tip, which can be inserted into a pipette seat designated by 20, which is formed in the valve body 12. The pipette tip 18 contains a sample to be analyzed, which can be coupled to the sample dispenser 10 by insertion into the pipette seat 20. For example, sample substance contained therein, in the embodiment shown in FIG. 1A in liquid form, can be inserted into a sample intake channel 22 formed in the valve body 12 by a corresponding operation of the pipette tip 18. It is also conceivable to provide a coupling mechanism which, when inserting the pipette tip 18 into the pipette 20, feeds the substance to be analyzed from the pipette tip 18 into the sample intake channel 22.

The sample intake channel 22 transverses the valve body 12 from one of the sides thereof, in which the pipette seat 20 is formed, to the opposite side, where it feeds into in an opening of the side surface. The sample intake channel 22 has a longitudinal axis D extending in the embodiment shown in FIG. 1a vertically downward from the pipette seat 20 arranged on the top side. The sample intake channel 22 transverses a substantially orthogonally extending cavity 24, which partitions the sample intake channel 22 into a first, top portion 22a and a second, bottom portion 22b.

The closing plug 16 serves to close the sample intake channel 22 from the end thereof opposite to the pipette seat 22. This end is in FIG. 1A, and typically also during operation, on the bottom such that the substance to be analyzed moves through the effect of gravity from the pipette seat 20 to the closing plug 16 traversing the cavity 24. The closing plug 16 is inserted into the second region 22b of the sample intake channel 22 and closes it in a fluid-tight manner. As will be shown, the volume of the sample intake channel 22 can be increased or decreased by moving the closing plug 16 in the feed direction of the axis D of the sample intake channel 22.

The actuator 14 has a cross-section that is circular about a longitudinal axis A, which coincides with a feed axis of the actuator 14 interacting with the valve body 12. As shown in the section in FIG. 1A containing the axis A, the actuator 14 has a front section 26 in a conical shape or frusto-conical shape and a substantially cylindrical rear section 28. The conical front section 26 is inclined relative to the axis A at a small angle of between 0 and 10 degrees.

The actuator 14 is associated with the cavity 24 formed in the valve body 12. The cavity 24 has a shape complementary to the actuator 14, i.e., it has a substantially cylindrical edge region 30, which terminates in a circular opening in the sidewall of the valve body 12. On the inside of the cylindrical edge region 30, a frusto-conical inner region 32 is arranged. The frusto-conical inner region is also inclined at an angle between 0 to 10 degrees relative to a central axis B of the cavity 24, in particular at the same angle as the frusto-conical front section 26 of the actuator 14. The central axis B defines the feed axis of the actuator 14 interacting with the valve body 12. The innermost region 36 of the cavity 24 is once more offset from the conically tapered shape of the inner region 32 towards the axis and forms a substantially cylindrical cavity having a smaller diameter than the diameter of the smaller base surface of the truncated cone. The actuator 14 may also be provided such as to be rotated relative to the valve body 12 about the feed axis in a predetermined manner and in relation up an increasing displacement in the feed direction by providing threads 62 in the region of the actuator interacting with the valve body.

In the front section 26 of the actuator 14, a channel 34 extending transversely, in particular orthogonally, to the axis A is formed axially right behind the base of the conical front region 26. The axis C of the channel 34 extends orthogonally to the axis A of the actuator. The channel 34 transverses the conical front region 26 of the actuator 14 from a lateral surface through the axis A up to the opposite lateral surface such that the longitudinal axis C of the channel intersects the axis A of the actuator. The volume occupied by this channel 34 is thus predefined by the geometry of the actuator 14 and can be determined very accurately. As will be explained in detail later, the channel 34 forms a metering chamber of the sample dispenser 10, by means of which a very precisely adjustable volume of a substance to be analyzed can be supplied to the analysis device.

Figure 1B:
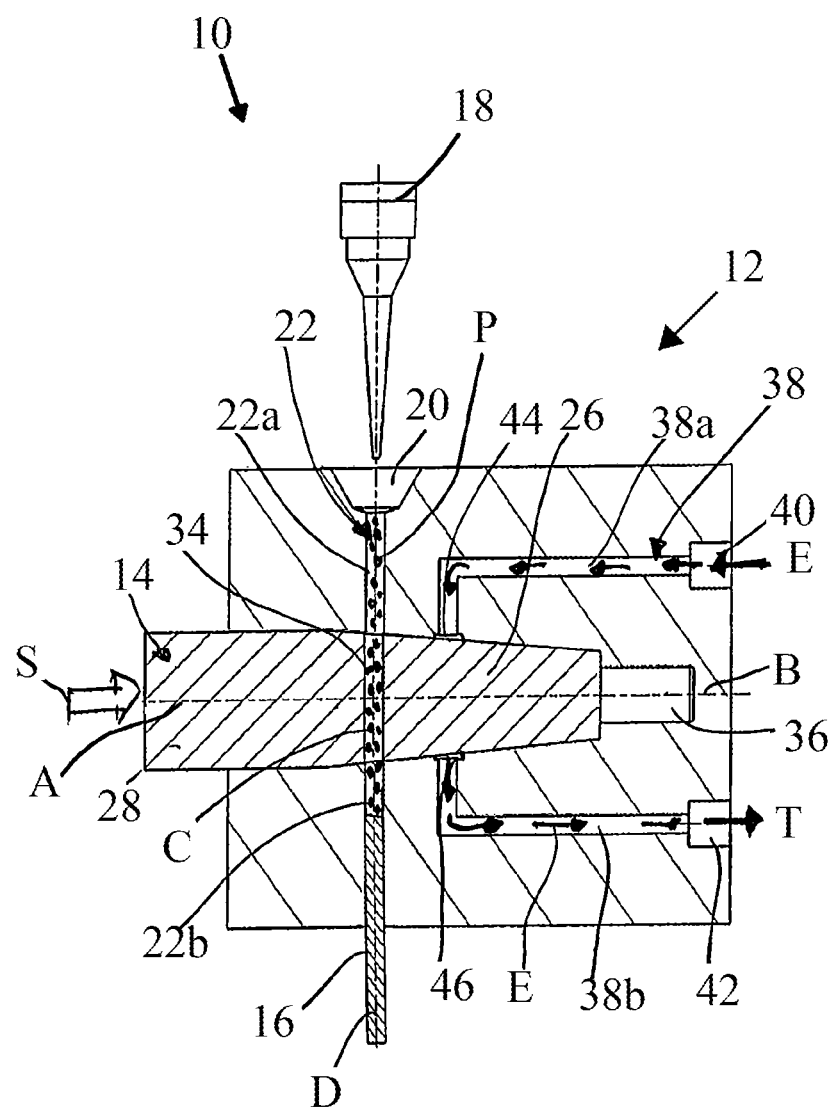
FIG. 1B shows another schematic illustration of the sample dispenser of FIG. 1A in the intake position.

At least when the actuator 14 is positioned in an intake position, as shown in FIG. 1B, the axes C and D of the transverse channel 34 formed in the actuator 14 and the sample intake channel 22 coincide and extend in particular vertically.

The valve body 12 further comprises a flow passage 38 extending between two opposite orifices 40, 42 at the opening of the cavity 24 associated with the actuator 14. The first orifice 40 is provided with an eluent reservoir (not shown) and forms an eluent inlet from which an eluent E flows to the sample dispenser 10. The term eluent is here generally used to describe a mobile phase to be supplied to the analysis device (to which, if applicable, the substance to be analyzed, herein referred to as sample P, is added during injection), in particular a liquid or gaseous phase. In the case of a chromatography device, the mobile phase flows around a stationary phase, which is hereinafter also referred to as the separating column. The second orifice 42 is connected to the analysis device T, in particular to the separating column of a gas chromatography (GC), liquid chromatography (LQ) or high performance liquid chromatography (HPLC) device, respectively. The second orifice 42 thus forms an outlet through which an eluent stream originating from the first orifice 40 (see arrow at E in FIG. 1A), or an eluent stream combined with the sample to be analyzed, can be supplied to the analysis device. The flow channel 38 is thus— depending on the position of the actuator 14 in the cavity 24 of the valve body 12—part of an eluent passage (in the intake position, see FIG. 1B) or a sample/eluent passage (in the injection position, see FIG. 1C).

The flow channel 38 connecting the eluent inlet 40 with the outlet 42 also transverses the cavity 24, however at a position, in the feed direction of the feed axis B, further inward than the sample intake channel 22. In the region between the orifices 44, 46 of the flow channel 38 opening into the cavity 24, the inner wall of the cavity 24 is provided with an annular groove 48 connecting the two orifices 44, 46. Instead of one completely circumferential annular groove 48, it would also be sufficient to provide an only approximately semi-circular groove connecting the two orifices 44, 46 on one side of the cavity 24.

The operation of the sample dispenser 10 will be explained in greater detail with reference to FIGS. 1B and 1C. FIG. 1B shows another schematic illustration of the sample dispenser 10 of FIG. 1A in the intake position. Intake position means that the sample dispenser is in this position ready to receive a sample, i.e., a substance to be analyzed, or, as indicated in FIG. 1B, already filled with the sample. The sample may be supplied by means of a suitably designed sample taking and treatment system, for example by means of a pipette tip 18 indicated in FIG. 1B. In the intake position, the actuator 14 is inserted into the cavity 24 and moved inwardly to the extent that the transverse channel 34 of the actuator 14 is aligned flush with the sample intake channel 22 of the valve body 12. The lower part 22b of the sample intake channel 22 is closed by the plug 16. Thus, the transverse channel 34 and the sample intake channel 22 together form a sample intake, in which the sample dispensed from the pipette tip 18 is collected (in FIG. 1, indicated by dots and designated by P). The level of the fluid collected in the sample intake is higher than the upper limit of the transverse channel 34. The transverse channel 34 thus forms a metering chamber with a precisely defined volume, as will be explained.

The geometries of the actuator 14 and the cavity 24 are formed complementary to one another and the actuator 14 is, in the intake position, inserted into the cavity 24 to an extent that the transition between the cylindrical section 28 and the conical section 26 of the actuator 14 coincides with the transition between the cylindrical region 30 and the conical region 32 of the cavity 24, or the actuator 14 is slightly pushed further towards the inside. The outer wall of the actuator 14 conically extending in the section 26 thus abuts the inner region 32 of the conically extending inner wall of the cavity 24 in a fluid-tight manner. A fluid-tight region, which closes the sample intake relative to the valve body 12 and the actuator 14, is thus formed between the actuator 14 and the valve body 12 around the sample intake, in particular around the regions where the upper sample intake channel section 22a and the lower sample intake channel section 22b, respectively, open into the metering chamber 34.

Also, in the region of the flow channel 38 connecting the two orifices 40 (eluent inlet) and 42 (eluent outlet), the outer wall of the actuator 14 abuts the inner wall of the cavity 24 in a fluid-tight manner. However, eluent E can flow between the two orifices 44, 46 through the groove 48 formed in the inner wall of the cavity 24 around the actuator 14 such that the eluent passage formed by the flow channel 38 and the groove 48 remains free in this position. In FIG. 1B, the eluent stream is indicated by arrows designated by E.

The eluent passage 38, 48 is, however, separated from the sample in a fluid-tight manner by having the actuating member 14 abutting the valve body 12 in the region between the eluent passage 38, 48 and the sample intake 22, 34 in a fluid-tight manner.

The movement of the actuator 14 in the feed direction may be realized by means of an actuating device, such as an electric servo drive, in FIG. 1B designated by S.

Figure 1C:
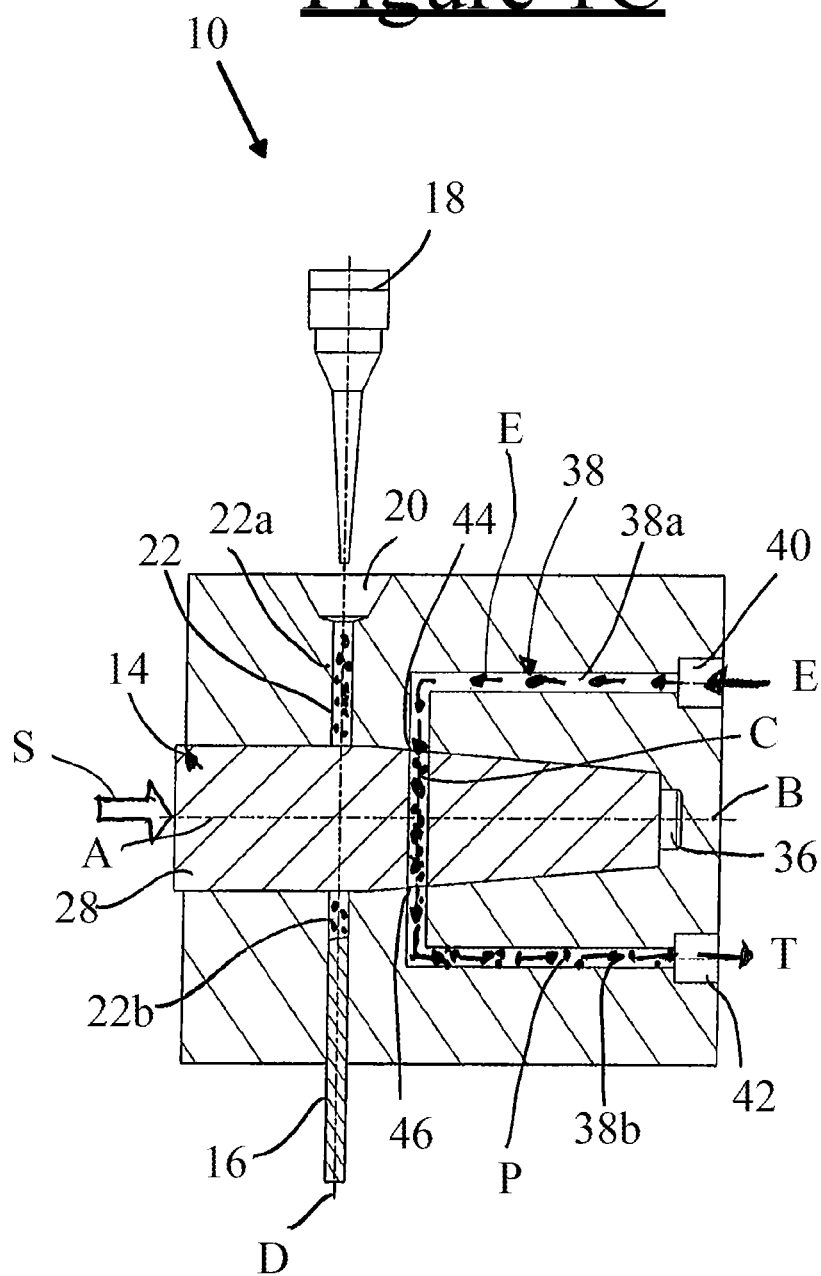
FIG. 1C shows another schematic illustration of the sample dispenser of FIG. 1A in the injection position.

FIG. 1C shows the sample dispenser 10 of FIGS. 1A and 1B in the injection position, in which the actuator 14 is, by means of the actuator drive S, further pressed into the inner region of the cavity 24 relative to the valve body 12. It can be seen that, in the injection position, the transverse channel 34 in the actuator 14, which now forms the metering chamber, is aligned flush with the two inner orifices 44, 46 of the flow channel 38. Thus, a sample/eluent passage has been formed, as the eluent E coming from the upper part 38a of the flow channel 38 (indicated by arrows in FIGS. 1B and 1C) mixes with the sample therein (indicated by dots in FIGS. 1B and 1C) when entering into the metering chamber 34 such that in the lower part 38b of the flow channel 38, ultimately a mixture of eluent E having the sample added thereto flows, which is finally supplied to the analysis device T via the outlet 42.

Moving the actuator 14 forward into the cavity 24 from the intake position (FIG. 1B) into the injection position (FIG. 1C) causes a deformation, in particular a plastic deformation, of at least the material of the valve body 12 surrounding the cavity 24. This can be gathered from the significantly shrunken innermost cylindrical portion 36 of the cavity 24 in FIG. 1C. The deformation is due to the pressing forces exerted by the actuator 14 causing a very close abutment between the actuator 14 and the valve body 12 in the region surrounding the sample-eluent passage 38a, 34, 38b. This close abutment ensures excellent fluid-tightness so that fluid conveyed through the sample-eluent-passage cannot escape. This allows for quantitative analyses with extremely high accuracy, as the sample volume conveyed to the analysis device T corresponds very exactly to the metering volume 34 prior to switching to the injection position.

In order to suppress a change in the metering volume 34 during switching from the intake position to the injection position to the greatest extent possible, it is recommended to make the actuator 14 of a considerably harder material than the valve body 12. For example, the actuator 14 can be made of ceramic, while for the valve body 12, mainly plastics such as PEEK (polyetheretherketone) are suitable. Pairings made of comparatively hard metal (e.g., stainless steel) or ceramics for the actuator, or soft metal (e.g., aluminum) or soft plastic for the valve body 12 are also an option.

The groove 48 described in detail with reference to FIG. 1A and still visible in FIG. 1B, which connects the two orifices 44, 46 of the flow channel, has, in the injection position of FIG. 1C, almost completely disappeared. This is due to the strong flow of material of the valve body 12 under the pressing force exerted by the actuator 14 when switching between the intake position and the injection position, with the result that the groove 48 has been practically completely filled with material of the valve body 12. In the injection position, the orifices 44, 46, which are not closed, thus get in fluid connection with the metering chamber 34, while the groove 48 practically no longer exists such that the entire eluent flowing in the upper flow channel section 38a flows through the metering chamber 34, where it is mixed with sample P.

Figure 2A:
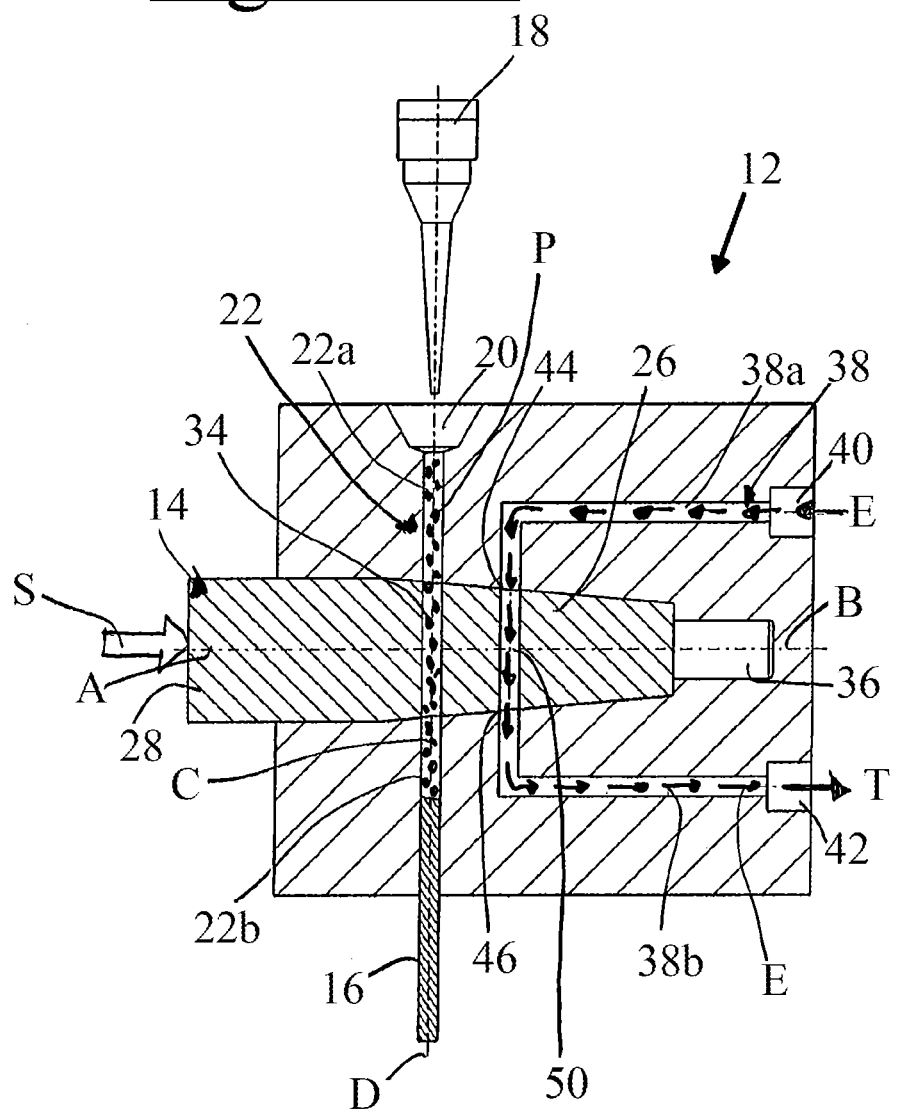
FIG. 2A shows a simplified schematic illustration of a second embodiment of a sample dispenser according to the invention in the intake position.

FIG. 2A shows a simplified schematic illustration of a second embodiment of a sample dispenser 10 according to the invention in the intake position. As mentioned above, only the differences compared to the embodiment shown in FIG. 1A to 1C will now be described, while regarding the remaining details, reference is made to the respective embodiment in FIGS. 1A to 1C. The embodiment according to FIG. 2A to 2C differs from the embodiment according to FIG. 1A to 1C only in that the eluent stream passes, in the intake position (FIG. 2A), between the orifice 44 of the upper flow channel section 38a opening into the cavity 24 and the orifice 46 of the lower flow channel section 38b opening into the cavity 24, through a further transverse channel 50 formed in the actuator 14. The transverse channel 50 is, in the intake position, aligned flush with the orifices 44, 46 such that the eluent passage is formed by the upper flow channel section 38a of the valve body 12, the other transverse channel 50 of the actuator and the lower flow channel section 38b of the valve body 12. The embodiment according to FIG. 2A to 2C thus requires the formation of two parallel extending transverse channels 34, 50 in the actuator 14, but has the advantage that when switching from the intake position to the injection position, lower pressing forces are required as, unlike in the embodiment of FIG. 1A to 1C, there is no necessity to fill a circumferential groove 48 by the flow of material of the valve body 12. It is sufficient to have the conically tapered outer wall of the actuator 14 abut the inner wall of the cavity 24 in a fluid-tight manner. Accordingly, only a very small cone angle can be sufficient to achieve the required fluid-tightness; in some cases, even a completely cylindrical actuator 14 interacting with an only slightly tapered cavity 24, or even a cylindrical cavity 24, can ensure sufficient fluid tightness.

Figure 2B:
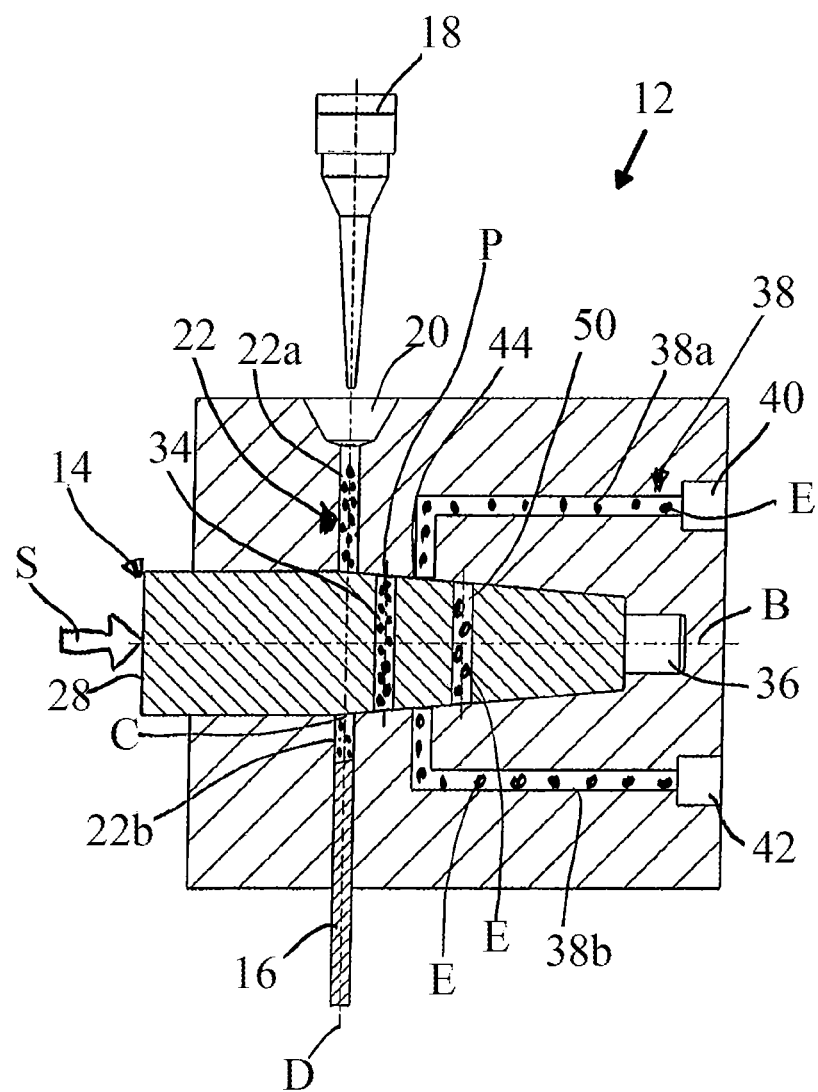
FIG. 2B shows another schematic illustration of the sample dispenser of FIG. 2A in an intermediate position between the intake position and the injection position.

FIG. 2B shows, for the second embodiment, an intermediate position of the injection valve arrangement between the intake position and the injection position. This intermediate position is assumed while switching the injection valve arrangement from the intake position to the injection position. In many cases, such an intermediate position will only be assumed as a transient state. There are, however, also applications, in particular those in which a single valve body 12 is associated with a plurality of actuators 14 (see for example FIG. 4A, 4B), where such intermediate position is assumed intentionally and the respective injection valve arrangement remains in the intermediate position.

It can be seen in FIG. 2B that in the intermediate position shown, both the first transverse channel forming the metering chamber 34 and the further transverse channel 50 of the actuator 14 abut respective regions of the conically tapered inner wall of the cavity 24. The actuating force exerted by the actuator drive S is selected such that both the metering chamber 34 containing sample P and the other transverse channel 50 containing the eluent E have their two open ends closed in a fluid-tight manner by the inner wall of the cavity 24. Thus, the injection valve arrangement is, in the intermediate position shown in FIG. 2B, completely inactive. It is neither possible for the sample to escape from the metering chamber 34 nor for the eluent to escape from the further transverse channel 50. The flow of eluent E between the eluent inlet 40 and the eluent outlet 42 is in this intermediate position also interrupted. However, this would not apply in the case of multiple injection valve arrangements, as long as at least one of these injection valve arrangements has a free eluent passage.

Figure 2C:
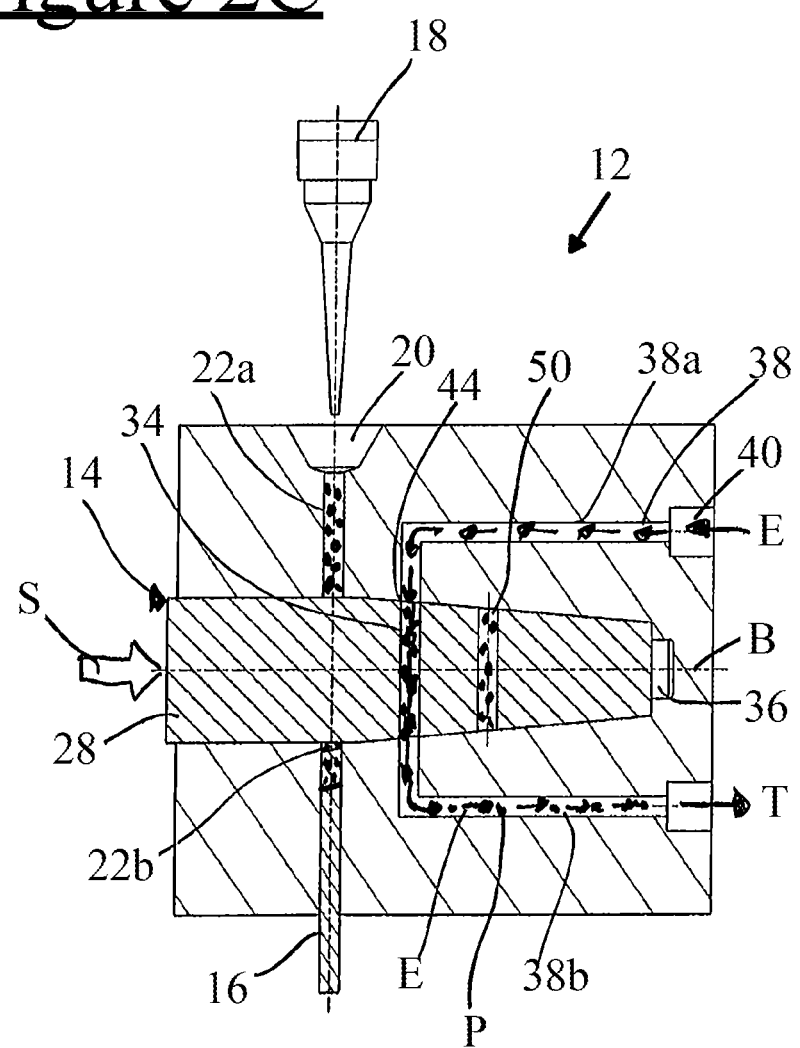
FIG. 2C shows a further schematic illustration of the sample dispenser of FIG. 2A in the injection position.

It is expressly pointed out that an intermediate position as shown in FIG. 2B may not only be provided in the embodiment according to FIGS. 2A to 2C, but readily also in the other embodiments. It makes sense to permanently assume this position in particular in case, as in the embodiment shown in FIG. 4A/4B, a plurality of actuators 14 are provided in a common injection valve arrangement. To suppress an interruption of the eluent stream in the intermediate position, a groove 48, as shown in FIG. 1A-1C, may, for example, additionally or alternatively to the passage 50, be provided in the inner wall of the valve body 12 surrounding the cavity 24.

It may even be advantageous to provide a further intermediate position, which, like the intermediate position shown in FIG. 2B, causes an interruption of the fluid connection between the inlet 40 and outlet 42, in which, however, the actuator 14 is, in the feed direction, inserted into the cavity 24 even beyond the injection position. The fluid-tightness of such a further intermediate position is in many cases better than when displacing the actuator 14 backwards opposite to the feed direction, in particular if irreversible effects, for example, plastic deformation of the valve body 12, occur during the insertion of the actuator 14 in the feed direction.

FIG. 2C shows a schematic illustration of the sample dispenser of FIG. 2A in the injection position. This largely corresponds to the situation shown in FIG. 1C. The metering chamber 34 containing the sample P has both of its open ends opening into the flow channel 38 such that the flow channel 38 and the metering chamber 34 together form the sample/eluent passage. The further transverse channel 50 has its two open ends abut the inner wall of the cavity 24 in a fluid-tight manner.

Figure 3A:
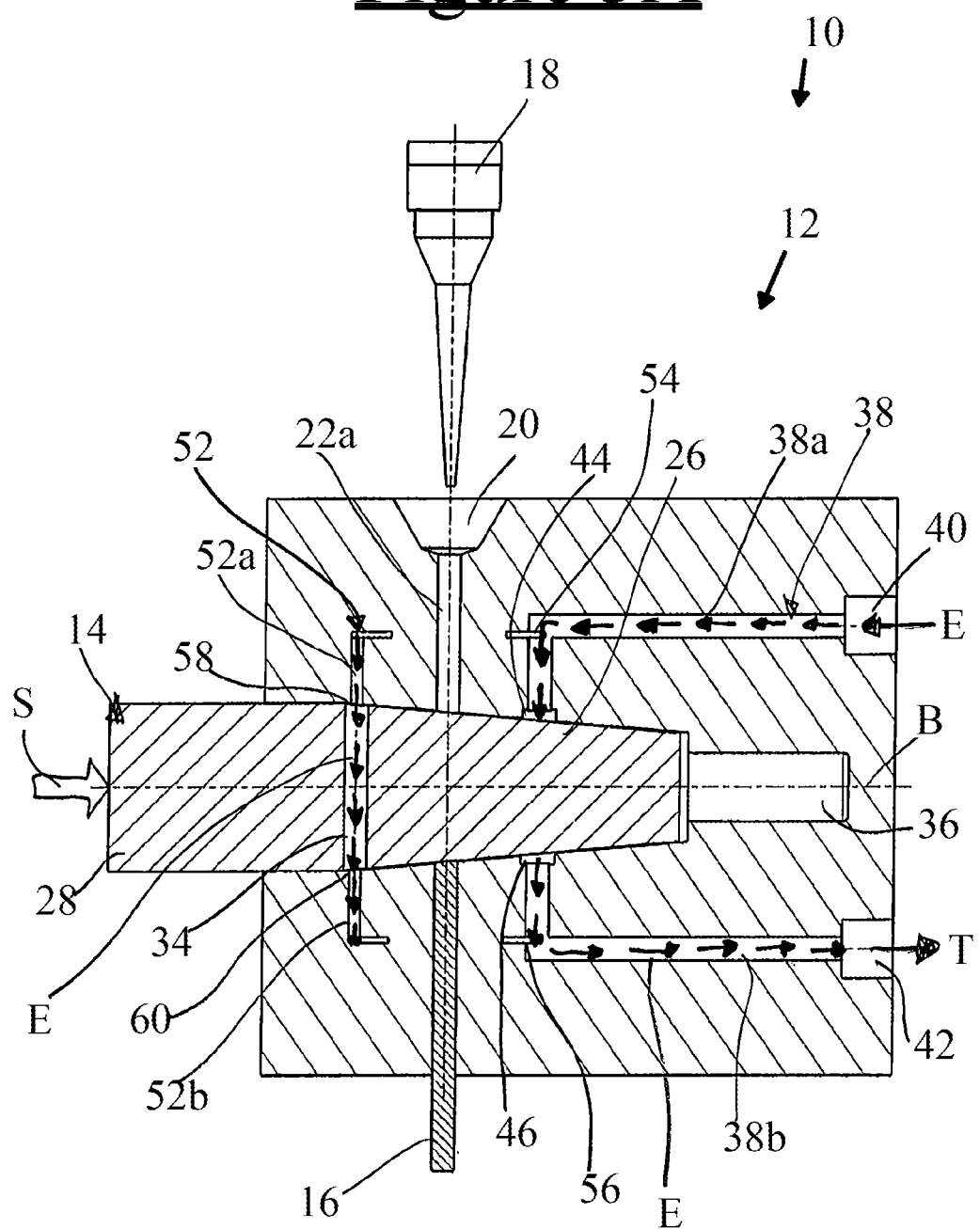
FIG. 3A shows a simplified schematic illustration of a third embodiment of a sample dispenser according to the invention in the prefill position.

FIG. 3A shows a simplified schematic illustration of a further embodiment of a sample dispenser 10 according to the invention. The sample dispenser 10 according to this embodiment is capable of receiving a sample to be analyzed only in a partial volume of the metering chamber 34, wherein the quantity of the sample can nevertheless be determined. To this end, the injection valve arrangement can be brought into an additional prefill position. FIG. 3A shows a simplified schematic illustration of the sample dispenser 10 in such a prefill position.

In the embodiment according to FIG. 3A to 3C, the valve body 12 comprises a prefill channel 52 branching off the flow channel 38. The prefill channel also traverses the cavity 24 formed in the valve body 12, which divides the prefill channel 52 into an upper prefill channel section 52a and a lower prefill channel section 52b. The upper prefill channel section 52a branches off the flow channel section 38a at a point upstream of the orifice 44 of the upper flow channel section 38a opening into the cavity 24, and the lower prefill channel section 52b opens into the flow channel section 38b at a point downstream of the orifice 46 of the lower flow channel section 38b opening into the cavity 24. The upper prefill channel section 52a surrounds the upper sample intake channel section 22a annularly. The lower prefill channel section 52b surrounds the lower sample intake channel section 22b annularly. Also in this case, it would be sufficient if the upper and the lower prefill channel sections 52a, 52b were formed in a semi-circular shape and passed through the upper and the lower sample intake channel section 22a, 22b only on one side.

In the prefill position shown in FIG. 3A, the actuator 14 is in a position such that the end 58 of the upper prefill channel section 52a opening into the cavity 24 is aligned flush with the one (upper) end of the transverse channel of the actuator 14 forming the metering chamber 34, and the opposite (lower) end of the transverse channel in turn opens into the end 60 of the lower prefill channel section 52b opening into the cavity 24. This results, in the prefill position, in an eluent passage which is formed by the two flow channel sections 38a, 38b together with the channel extending between the actuator 14 and the annular groove 48 in the inner wall of the cavity 24 (as in the embodiment shown in FIG. 1) and the two prefill channel sections 52a, 52b together with the transverse channel formed in the actuator 14, which forms the metering chamber 34.

If the injection valve arrangement is switched to the intake position shown in FIG. 3B, the transverse channel of the actuator 14 forming the metering chamber 34 then opens into the upper and the lower sample intake channel sections 22a, 22b, as in the previously discussed embodiments. However, in the embodiment of FIG. 3A to 3C, the metering chamber 34 is, in this position, completely filled with eluent E. Therefore, the volume of the sample intake formed by the metering chamber 34, the upper sample intake channel section 22a and the lower sample intake channel section 22b is enlarged by pulling the closing plug 16 out. In FIG. 3B, the closing plug 16 moves a little down along the axis D when it is pulled out, as indicated by the downward-pointing arrow. The increase in the volume of the sample intake can be readily determined on the basis of the displacement of the closing plug 16. Since eluent E in the metering chamber flows into the space that becomes free by pulling the plug 16 back, the metering chamber 34 then has a volume corresponding to this increase available for receiving the sample P. Now sample is again fed into the metering chamber 34 via the pipette seat 20 (whereupon the metering chamber 34 is again overfilled) and then the injection valve arrangement is moved into the injection position shown in FIG. 3C. This is realized in exactly the same manner as in the embodiment shown in FIG. 1A to 1C, with the difference that the metering chamber now contains a mixture of sample P to be analyzed and eluent E, which mixes with the eluent flowing in the flow channel 38.

FIG. 4 shows a simplified schematic illustration of a fourth embodiment of a sample dispenser 10 according to the invention. As mentioned above, only the differences compared to the previously described embodiments are described, while regarding the remaining details, reference is made to the respective embodiments mentioned above. The sample dispenser 10 shown in FIG. 4 comprises a plurality of actuators 14A, 14B, 14C, 14D. Each of the actuators 14A, 14B, 14C, 14D is associated with a respective injection valve arrangement. Each injection valve arrangement also comprises a valve body 12A, 12B, 12C, 12D and a valve seat 20A, 20B, 20C, 20D. Each valve seat 20A, 20B, 20C, 20D is associated with a pipette tip 18A, 18B, 18C, 18D. The injection valve arrangements according to FIG. 4 may be constructed in accordance with any of the embodiments described above. In the situation shown in FIG. 4, the actuator 14A of the first injection valve is positioned in the intake position and the other actuators 14B, 14C, 14D are still in a state prior to insertion into the respectively associated cavity of the valve body 12B, 12C, 12D.

In the configuration shown in FIG. 4, each injection valve arrangement comprises its own valve body 12A, 12B, 12C, 12D, that is, each actuator 14A, 14B, 14C, 14D is associated with its own valve body 12A, 12B, 12C, 12D. Nevertheless, all injection valve arrangements are combined in the sense that overall only one single inlet for the eluent and one single outlet to the analysis device is provided. It would also be possible to associate all the actuators 14A, 14B, 14C, 14D to only one single common valve body 12. It is understood that in this way, any number of injection valve arrangements or actuators may be provided. In this case, it is advantageous if the individual injection valve arrangements or actuators can permanently move into an intermediate position after injection, as shown in FIG. 2B, as cross-contamination effects can be effectively suppressed this way. This intermediate position may also be assumed by further displacing the respective actuator 14A, 14B, 14C, 14D in the feed direction beyond the injection position, as has been already mentioned above with reference to FIG. 2B.

The various embodiments described above can be combined to provide further embodiments. These and other changes can be made to the embodiments in light of the above-detailed description. In general, in the following claims, the terms used should not be construed to limit the claims to the specific embodiments disclosed in the specification and the claims, but should be construed to include all possible embodiments along with the full scope of equivalents to which such claims are entitled. Accordingly, the claims are not limited by the disclosure.

The invention claimed is:

1. A sample dispenser for an analysis device, the sample dispenser comprising:
a sample intake configured to receive a sample to be analyzed,
an inlet configured to receive an eluent,
an outlet configured to output at least one of the eluent and a mixture of at least part of the sample and the eluent, and
an injection valve arrangement configured to switch from an intake position to an injection position,
wherein, in the intake position, the inlet is in fluid communication with the outlet to deliver the eluent, and in the injection position, the inlet is in fluid communication with the outlet to deliver the mixture,
wherein, in the intake position, the sample intake is in a fluid-tight manner separated from the eluent and
wherein, in the injection position, the at least part of the sample in the sample intake combines with the eluent,
wherein the sample dispenser is configured as a disposable component for single use only.

2. The sample dispenser according to claim 1, further comprising a sample port, wherein in the intake position of the injection valve arrangement, the sample to be analyzed is received through the sample port.

3. The sample dispenser according to claim 1, wherein the injection valve arrangement comprises a valve body and an actuator that is moveable relative to the valve body, wherein at least one of the valve body and the actuator includes the sample intake, the inlet, and the outlet.

4. The sample dispenser according to claim 3, wherein the sample intake is at least partly formed in the actuator.

5. The sample dispenser according to claim 3, further comprising an actuating drive configured to act upon the actuator.

6. The sample dispenser according to claim 3, wherein at least one flow channel is formed in the valve body, wherein the at least one flow channel forms, in the intake position of the actuator, an eluent passage between the inlet and the outlet, and wherein the at least one flow channel and the actuator together form, in the injection position of the injection valve arrangement, an eluent passage between the inlet and the outlet.

7. The sample dispenser according to claim 1, wherein the injection valve arrangement is configured to be switched to another position in which there is no fluid connection between the inlet and the outlet.

8. The sample dispenser according to claim 3, wherein the valve body comprises a cavity configured to receive the actuator.

9. The sample dispenser according to claim 3, wherein the sample intake comprises a metering chamber formed in the actuator or between the actuator and the valve body, wherein in the intake position of the injection valve arrangement, the metering chamber is in fluid communication with a sample port.

10. The sample dispenser according to claim 9, wherein the metering chamber comprises a predetermined volume.

11. The sample dispenser according to claim 10, wherein at least one of a volume of the sample intake and the volume of the metering chamber is adjustable.

12. The sample dispenser according to claim 11, comprising at least one plug for adjusting at least one of the volume of the sample intake and the volume of the metering chamber.

13. The sample dispenser according to claim 9, wherein at least one of the sample intake and the metering chamber is configured to be prefilled with eluent.

14. The sample dispenser according to claim 13, wherein the injection valve arrangement is configured to be switched from a prefilling position, in which the metering chamber, is in fluid connection with the eluent stream, to the intake position.

15. The sample dispenser according to claim 12, wherein, in the intake position, the at least one plug acts on at least one of the sample intake and the metering chamber to change the respective volume thereof.

16. The sample dispenser according to claim 3, wherein in the actuator or between the actuator and the valve body, at least one fluid connection is formed, wherein in the intake position of the injection valve arrangement, eluent is able flow from the inlet to the outlet through the at least one fluid connection.

17. The sample dispenser according to claim 6, wherein, at least in the intake position of the injection valve arrangement, the actuator interacts with the valve body such that the sample intake and the eluent passage are separated from one another in a fluid-tight manner.

18. The sample dispenser according to claim 3, wherein the actuator is configured to be moved relative to the valve body such that, in the injection position of the injection valve arrangement, a flow channel formed in the valve body becomes in fluid communication with the inlet and the outlet.

19. The sample dispenser according to claim 18, wherein the actuator can be moved relative to the valve body along a feed direction in an axial direction to switch the injection valve arrangement from the intake position to the injection position.

20. The sample dispenser according to claim 3, wherein the actuator is, relative to the valve body, in a pressing seat such that when switching the actuator from the intake position to the injection position, the pressing forces do not decrease.

21. The sample dispenser according to claim 20, wherein a region of the actuator interacting with the valve body has a shape that is tapered in a feed direction of the actuator.

22. The sample dispenser according to claim 20, wherein in response to switching the injection valve arrangement from the intake position to the injection position, a deformation of at least the valve body occurs.

23. The sample dispenser according to claim 22, wherein the deformation is at least partially a plastic deformation.

24. The sample dispenser according to claim 3, wherein a region of the actuator interacting with the valve body is configured such that a rotation of the actuator relative to the valve body is suppressed.

25. The sample dispenser according to claim 8, wherein a region of the actuator that is received by the cavity of the valve body has threads.

26. The sample dispenser according to claim 3, wherein the actuator is made of a harder material than the valve body.

27. The sample dispenser according to claim 1, comprising a plurality of actuators and a plurality of sample intakes, wherein each of the actuators is associated with a respective one of the plurality of sample intakes.

28. The sample dispenser according to claim 27, wherein the inlet and the outlet are associated with each of the actuators.

* * * * *